United States Patent
Jang et al.

(10) Patent No.: US 8,449,435 B2
(45) Date of Patent: May 28, 2013

(54) GUIDING EXERCISE BASED ON FAT OXIDATION RATE

(75) Inventors: Seungjin Jang, Gyeonggi-Do (KR); Gyuseog Hong, Chungcheongnam-Do (KR); Jeongmee Koh, Seoul (KR); Youngdon Hwang, Seoul (KR)

(73) Assignee: LG Electronics Inc., Seoul (KR)

( * ) Notice: Subject to any disclaimer, the term of this patent is extended or adjusted under 35 U.S.C. 154(b) by 263 days.

(21) Appl. No.: 13/047,407

(22) Filed: Mar. 14, 2011

(65) Prior Publication Data

US 2012/0238832 A1  Sep. 20, 2012

(51) Int. Cl.
*A63B 24/00* (2006.01)

(52) U.S. Cl.
USPC .................. 482/9; 482/1; 482/901; 601/2

(58) Field of Classification Search
USPC ............... 482/1–9, 900–902; 434/247; 601/1, 601/2, 23; 600/300, 481
See application file for complete search history.

(56) References Cited

U.S. PATENT DOCUMENTS

| | | | |
|---|---|---|---|
| 7,534,206 B1 * | 5/2009 | Lovitt et al. | 600/300 |
| 2010/0286534 A1 * | 11/2010 | Greenberg | 600/484 |
| 2013/0012840 A1 * | 1/2013 | Feferberg | 601/2 |

* cited by examiner

*Primary Examiner* — Glenn Richman
(74) *Attorney, Agent, or Firm* — Birch, Stewart, Kolasch & Birch, LLP

(57) ABSTRACT

Disclosed is An exercise guide apparatus comprising: a sensing unit configured to obtain a heart rate of a subject; a strength determining unit configured to determine a maximal oxygen uptake of the subject; an exercise intensity measurement unit configured to determine a current exercise intensity of the subject based on the heart rate obtained by the sensing unit; and an exercise guide unit configured to estimate a fat oxidation rate of the subject, determine whether or not fat oxidation of the subject occurs, generate guide information according to a result of the determination of the occurrence of fat oxidation, and display the guide information generated, wherein the fat oxidation rate is estimated based on a ratio of fat being oxidized at the current exercise intensity to the maximal oxygen uptake, and wherein the occurrence of fat oxidation is determined by checking whether or not the fat oxidation rate estimated is greater than a threshold.

12 Claims, 7 Drawing Sheets

GUIDING EXERCISE BASED ON FAT OXIDATION RATE

TECHNICAL FIELD

The present disclosure relates to guiding exercise, and more particularly, to providing exercise guide information based on a fat oxidation rate.

BACKGROUND ART

Recently, interest in an exercise activity for wellness maintenance, health recovery, and fitness (or strength building) is increasing. The differences of the physical condition, body strength, athletic position and exercise purpose between individuals require appropriate exercise methods for each individual who does an exercise activity. In addition, in order to help such exercise activities, electronic devices each having a sensor is increasingly used.

DISCLOSURE OF THE INVENTION

Therefore, the present disclosure is to provide an exercise guide apparatus and an exercise guide method providing an exercise intensity and an exercise pattern based on a fat oxidation rate.

Also, the present disclosure is to provide a method for estimating a fat oxidation rate to generate exercise guide information without using a method of analyzing a respiratory gas.

In one aspect, an exercise guide apparatus is described. The exercise guide apparatus comprises a sensing unit configured to obtain a heart rate of a subject; a strength determining unit configured to determine a maximal oxygen uptake of the subject; an exercise intensity measurement unit configured to determine a current exercise intensity of the subject based on the heart rate obtained by the sensing unit; and an exercise guide unit configured to estimate a fat oxidation rate of the subject, determine whether or not fat oxidation of the subject occurs, generate guide information according to a result of the determination of the occurrence of fat oxidation, and display the guide information generated, wherein the fat oxidation rate is estimated based on a ratio of fat being oxidized at the current exercise intensity to the maximal oxygen uptake, and wherein the occurrence of fat oxidation is determined by checking whether or not the fat oxidation rate estimated is greater than a threshold.

This, and other aspects, can include one or more of the following features. If the fat oxidation is determined not to occur, the guide information generated by the exercise guide may indicate that the current exercise intensity is not optimal for fat oxidation. The exercise guide unit may select a fat oxidation curve corresponding to characteristic information of the subject from a database containing fat oxidation patterns, and can estimate the fat oxidation rate by using the fat oxidation curve selected. The apparatus may further comprises an input unit configured to receive an input signal, wherein the exercise guide unit prepares the database containing the fat oxidation patterns by characteristic information, receives characteristic information of the subject by the input signal, and selects the fat oxidation curve corresponding to the characteristic information received from the database, and wherein the characteristic information of the subject is at least one of gender, age, and weight. The apparatus may further comprises a timer unit configured to accumulate a time, wherein if the fat oxidation is determined to occur, the exercise guide unit obtains the accumulated total time of the heart rate obtainment from the timer unit, calculates an accumulated fat oxidation during the accumulated total time, and displays the accumulated fat oxidation, and wherein the accumulated fat oxidation is calculated by using a value on the fat oxidation curve corresponding to the fat oxidation rate estimated. The strength determining unit may determine the maximal oxygen uptake based on a maximum heart rate of the subject. The sensing unit may obtain the heart rate of the subject from an electrocardiogram sensor.

In another aspect, a method for providing exercise guide information is described. The method comprises obtaining a heart rate of a subject; determining a current exercise intensity of the subject based on the heart rate; determining a maximal oxygen uptake of the subject; estimating a fat oxidation rate of the subject, the fat oxidation rate indicating a ratio of fat being oxidized at the current exercise intensity to the maximal oxygen uptake; determining whether or not fat oxidation of the subject occurs by checking whether or not the fat oxidation rate estimated is greater than a threshold; generating guide information according to a result of the determination of the occurrence of fat oxidation; and displaying the guide information.

This, and other aspects, can include one or more of the following features. If the fat oxidation is determined not to occur, the guide information generated may indicate that the current exercise intensity is not optimal for fat oxidization. The estimating of the fat oxidation rate may comprise selecting a fat oxidation curve corresponding to characteristic information of the subject from a database containing fat oxidation patterns; and determining whether or not the fat oxidation rate estimated is greater than a threshold on the fat oxidation curve selected. The selecting the fat oxidation curve may further comprise preparing the database containing the fat oxidation patterns by characteristic information; and receiving characteristic information of the subject by an input signal, wherein the characteristic information of the subject is at least one of gender, age, and weight. The method may further comprise obtaining an accumulated total time of the heart rate obtainment if the fat oxidation is determined to occur; calculating an accumulated fat oxidation during the accumulated total time by using a value on the fat oxidation curve corresponding to the fat oxidation rate estimated; and displaying the accumulated fat oxidation.

In the exercise guide apparatus and method for providing exercise guide information according to exemplary embodiments of the present disclosure, fat oxidation rate of a subject can be estimated by using heart rate information of the subject.

In addition, in the exercise guide apparatus and method for providing exercise guide information according to exemplary embodiments of the present disclosure, it is determined whether or not fat oxidation rate is effectively made based on an estimated fat oxidation rate, thereby providing exercise guide information allowing for the user to determine whether to change or maintain his exercise intensity and exercise pattern.

The foregoing and other objects, features, aspects and advantages of the present invention will become more apparent from the following detailed description of the present invention when taken in conjunction with the accompanying drawings.

BRIEF DESCRIPTION OF THE DRAWINGS

The details of one or more implementations are set forth in the accompanying drawings and the description below. Other features will be apparent from the description and drawings, and from the claims.

MODES FOR CARRYING OUT THE PREFERRED EMBODIMENTS

The terms used in the present application are merely used to describe particular embodiments, and are not intended to limit the present invention.

It should be understood that the following exemplifying description of the invention is not intended to restrict the invention to specific forms of the present invention but rather the present invention is meant to cover all modifications, similarities and alternatives which are included in the spirit and scope of the present invention.

Like numbers refer to like elements throughout, and a repeated description will be omitted. In the following description, usage of suffixes such as 'module', 'part' or 'unit' used for referring to elements is given merely to facilitate explanation of the present invention, without having any significant meaning by itself.

The present invention is not limited by the exemplary embodiments described hereinafter.

Exemplary embodiments of the present invention will be described.

Figure 1:
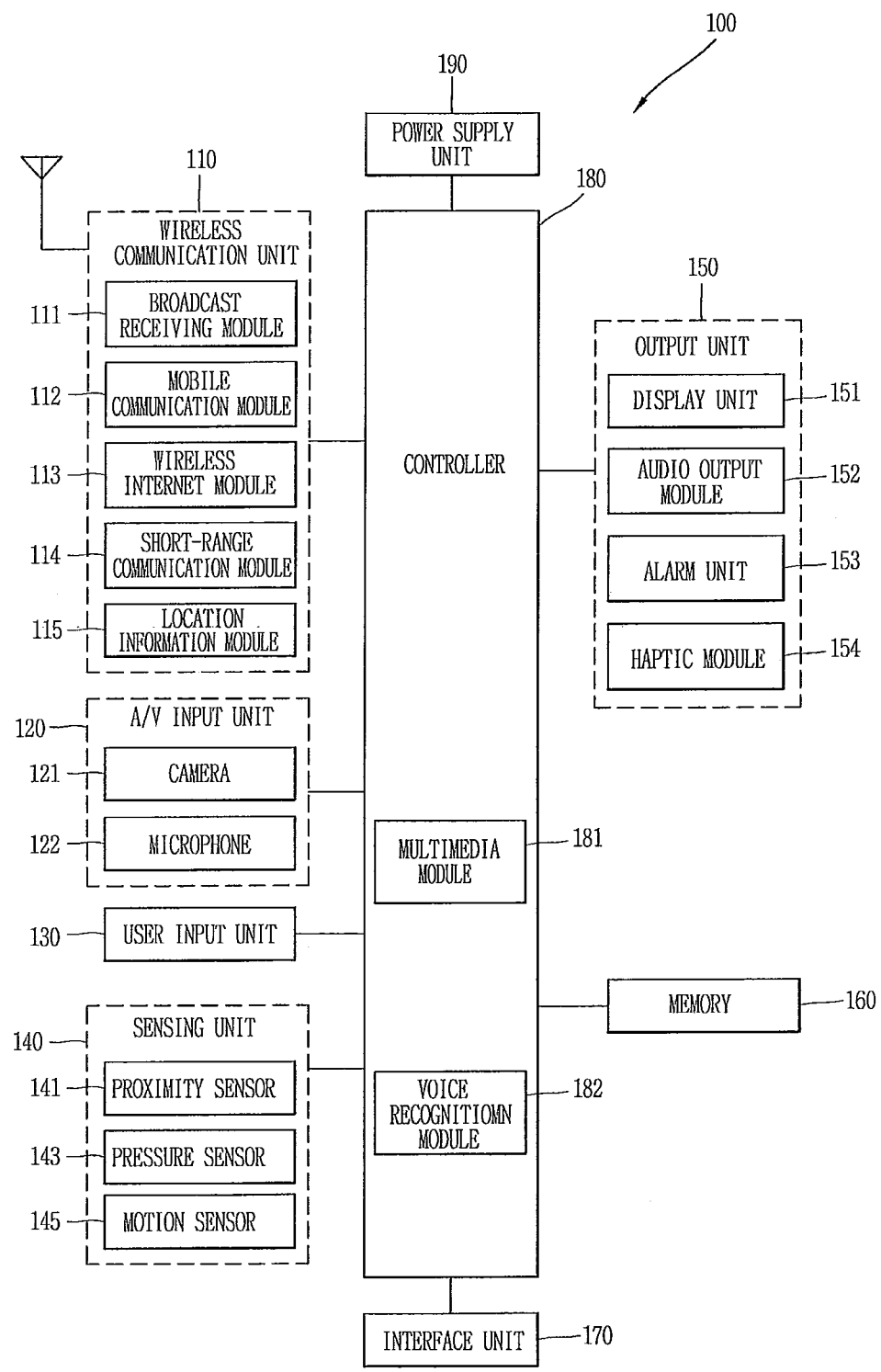
FIG. 1 is a schematic block diagram of a mobile terminal.

FIG. 1 is a schematic block diagram of a mobile terminal according to an exemplary embodiment of the present invention.

The mobile terminal described in the present invention may include mobile phones, smart phones, notebook computers, digital broadcast receivers, PDAs (Personal Digital Assistants), PMPs (Portable Multimedia Player), navigation devices, and the like. It would be understood by a person in the art that the configuration according to the embodiments of the present invention can be also applicable to the fixed types of terminals such as digital TVs, desk top computers, or the like, except for any elements especially configured for a mobile purpose.

As shown in FIG. 1, a mobile terminal (or a mobile phone) 100 may include a wireless communication unit 110, an A/V (Audio/Video) input unit 120, a user input unit 130, a sensing unit 140, an output unit 150, a memory 160, an interface unit 170, a controller 180, and a power supply unit 190, etc.

FIG. 1 shows the mobile terminal as having various components, but it should be understood that implementing all of the illustrated components is not a requirement. Greater or fewer components may alternatively be implemented.

The wireless communication unit 110 typically includes one or more components allowing radio communication between the mobile terminal 100 and a wireless communication system or a network in which the mobile terminal is located. For example, the wireless communication unit may include at least one of a broadcast receiving module 111, a mobile communication module 112, a wireless Internet module 113, a short-range communication module 114, and a location information module 115.

The broadcast receiving module 111 receives broadcast signals and/or broadcast associated information from an external broadcast management server (or other network entity) via a broadcast channel. The broadcast channel may include a satellite channel and/or a terrestrial channel. The broadcast management server may be a server that generates and transmits a broadcast signal and/or broadcast associated information or a server that receives a previously generated broadcast signal and/or broadcast associated information and transmits the same to a terminal. The broadcast signal may include a TV broadcast signal, a radio broadcast signal, a data broadcast signal, and the like. Also, the broadcast signal may further include a broadcast signal combined with a TV or radio broadcast signal.

The broadcast associated information may also be provided via a mobile communication network and, in this case, the broadcast associated information may be received by the mobile communication module 112. The broadcast associated information may exist in various forms. For example, it may exist in the form of an electronic program guide (EPG) of digital multimedia broadcasting (DMB), electronic service guide (ESG) of digital video broadcast-handheld (DVB-H), and the like.

The broadcast receiving module 111 may be configured to receive signals broadcast by using various types of broadcast systems. In particular, the broadcast receiving module 111 may receive a digital broadcast by using a digital broadcast system such as multimedia broadcasting-terrestrial (DMB-T), digital multimedia broadcasting-satellite (DMB-S), digital video broadcast-handheld (DVB-H), the data broadcasting system known as media forward link only (MediaFLO®), integrated services digital broadcast-terrestrial (ISDB-T), etc. The broadcast receiving module 111 may be configured to be suitable for every broadcast system that provides a broadcast signal as well as the above-mentioned digital broadcast systems. Broadcast signals and/or broadcast-associated information received via the broadcast receiving module 111 may be stored in the memory 160 (or anther type of storage medium).

The mobile communication module 112 transmits and/or receives radio signals to and/or from at least one of a base station (e.g., access point, Node B, etc.), an external terminal (e.g., other user devices) and a server (or other network entities). Such radio signals may include a voice call signal, a video call signal or various types of data according to text and/or multimedia message transmission and/or reception.

The wireless Internet module 113 supports wireless Internet access for the mobile terminal. This module may be internally or externally coupled to the terminal. The wireless Internet access technique implemented may include a WLAN (Wireless LAN) (Wi-Fi), Wibro (Wireless broadband), WiMax (World Interoperability for Microwave Access), HSDPA (High Speed Downlink Packet Access), or the like.

The short-range communication module 114 is a module for supporting short range communications. Some examples of short-range communication technology include Bluetooth™, Radio Frequency IDentification (RFID), Infrared Data Association (IrDA), Ultra-WideBand (UWB), ZigBee™, Wireless LAN (protocols such as Bluetooth, 802.11, etc.), and the like.

The location information module 115 is a module for checking or acquiring a location (or position) of the mobile terminal. A typical example of the location information module is a GPS (Global Positioning System). For example, the GPS module may measure an accurate time and distance from three or more satellites, and accurately calculate a current location of the mobile communication terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites. As the location information module 233, a Wi-Fi position system and/or hybrid positioning system may be used.

The A/V input unit 120 is configured to receive an audio or video signal. The A/V input unit 120 may include a camera 121 (or other image capture device) and a microphone 122 (or other sound pick-up device). The camera 121 processes image data of still pictures or video obtained by an image capture device in a video capturing mode or an image capturing mode. The processed image frames may be displayed on a display unit 151 (or other visual output device).

The image frames processed by the camera 121 may be stored in the memory 160 (or other storage medium) or transmitted via the wireless communication unit 110. Two or more cameras 121 may be provided according to the configuration of the mobile terminal.

The microphone 122 may receive sounds (audible data) via a microphone (or the like) in a phone call mode, a recording mode, a voice recognition mode, and the like, and can process such sounds into audio data. The processed audio (voice) data may be converted for output into a format transmittable to a mobile communication base station (or other network entity) via the mobile communication module 112 in case of the phone call mode. The microphone 122 may implement various types of noise canceling (or suppression) algorithms to cancel (or suppress) noise or interference generated in the course of receiving and transmitting audio signals.

The user input unit 130 (or other user input device) may generate input data from commands entered by a user to control various operations of the mobile terminal. The user input unit 130 may include a keypad, a dome switch, a touch pad (e.g., a touch sensitive member that detects changes in resistance, pressure, capacitance, etc. due to being contacted) a jog wheel, a jog switch, and the like. In particular, when the touch pad is overlaid with the display unit 151 in a layered manner, it may be called a touch screen.

The sensing unit 140 (or other detection means) detects a current status (or state) of the mobile terminal 100 such as an opened or closed state of the mobile terminal 100, a location of the mobile terminal 100, the presence or absence of user contact with the mobile terminal 100 (i.e., touch inputs), the orientation of the mobile terminal 100, an acceleration or deceleration movement and direction of the mobile terminal 100, etc., and generates commands or signals for controlling the operation of the mobile terminal 100. For example, when the mobile terminal 100 is implemented as a slide type mobile phone, the sensing unit 140 may sense whether the slide phone is opened or closed. In addition, the sensing unit 140 can detect whether or not the power supply unit 190 supplies power or whether or not the interface unit 170 is coupled with an external device.

The sensing unit 140 may include a proximity sensor 141, a pressure sensor 143, a motion sensor 145, or the like. The proximity sensor 141 detects an object approaching the mobile terminal 100 or the presence or absence of an object existing near the mobile terminal 100, or the like, without a physical contact. The proximity sensor 141 may detect a proximity object by using a change in an AC magnetic field or a change in a static magnetic field, or by using a variation of capacitance, or the like. Two or more proximity sensors 141 may be provided according to specifications.

The pressure sensor 143 can detect whether or not pressure is applied to the mobile terminal 100, the size of the pressure, or the like. The pressure sensor 143 may be installed at a portion of the mobile terminal 100 where pressure needs to be detected according to a usage environment. When the pressure sensor 143 is installed on the display unit 151, a touch input through the display unit 151 and a pressure touch input to which greater pressure than the touch input is applied can be identified according to a signal output from the pressure sensor 143. Also, when a pressure touch is input, the size of the pressure applied to the display unit 151 can be recognized according to a signal output from the pressure sensor 143.

The motion sensor 145 detects the location or a movement of the mobile terminal 100 by using an acceleration sensor, a gyro sensor, or the like. An acceleration sensor which can be used for the motion sensor 145 is an element for changing a change in acceleration in one direction into an electrical signal, which is widely used in line with the development of an MEMS (micro-electromechanical systems). The acceleration sensor includes a sensor which is installed in an airbag system of a vehicle so as to be used to measure an acceleration of a large value used to detect a collision, a sensor which recognizes a fine manipulation of a human being's hand to measure an acceleration of a fine value used as an input unit such as games or the like. The acceleration sensor is configured by mounting a 2-axis acceleration sensor or a 3-axis acceleration sensor on a single package, and only a single axis, i.e., Z axis, may be required according to usage environments. Thus, when an X-axis or Y-axis directional acceleration sensor is to be used, instead of the Z-axis directional acceleration sensor for some reasons, the acceleration sensor may be mounted to be stood on a main substrate by using a piece substrate.

Also, the gyro sensor measures an angular velocity, which can be detect a direction which has been rotated with respect to a reference direction.

The output unit 150 is configured to provide outputs in a visual, audible, and/or tactile manner (e.g., audio signal, video signal, alarm signal, vibration signal, etc.). The output unit 150 may include the display unit 151, an audio output module 152, an alarm unit 153, a haptic module 154, and the like.

The display unit 151 may display (output) information processed in the mobile terminal 100. For example, when the mobile terminal 100 is in a phone call mode, the display unit 151 may display a User Interface (UI) or a Graphic User Interface (GUI) associated with a call or other communication (such as text messaging, multimedia file downloading, etc.). When the mobile terminal 100 is in a video call mode or image capturing mode, the display unit 151 may display a captured image and/or received image, a UI or GUI that shows videos or images and functions related thereto, and the like.

The display unit 151 may include at least one of a Liquid Crystal Display (LCD), a Thin Film Transistor-LCD (TFT-LCD), an Organic Light Emitting Diode (OLED) display, a flexible display, a three-dimensional (3D) display, or the like. Some of them may be configured to be transparent or light-transmissive to allow viewing of the exterior, which may be called transparent displays. A typical transparent display may be, for example, a TOLED (Transparent Organic Light Emitting Diode) display, or the like.

The mobile terminal 100 may include two or more display units (or other display means) according to its particular desired embodiment. For example, a plurality of display units may be separately or integrally disposed on one surface of the mobile terminal, or may be separately disposed on mutually different surfaces.

Meanwhile, when the display unit 151 and a sensor (referred to as a 'touch sensor', hereinafter) for detecting a touch operation are overlaid in a layered manner to form a touch screen, the display unit 151 may function as both an input device and an output device. The touch sensor may have a form of a touch film, a touch sheet, a touch pad, and the like.

The touch sensor may be configured to convert pressure applied to a particular portion of the display unit 151 or a change in the capacitance or the like generated at a particular portion of the display unit 151 into an electrical input signal. The touch sensor may be configured to detect the pressure when a touch is applied, as well as the touched position and area. When there is a touch input with respect to the touch sensor, a corresponding signal (signals) are transmitted to a touch controller. The touch controller processes the signals and transmits corresponding data to the controller 180. Accordingly, the controller 180 may recognize which portion of the display unit 151 has been touched.

The proximity sensor 141 may be disposed within or near the touch screen. The proximity sensor 141 is a sensor for detecting the presence or absence of an object relative to a certain detection surface or an object that exists nearby by using the force of electromagnetism or infrared rays without a physical contact. Thus, the proximity sensor 141 has a considerably longer life span compared with a contact type sensor, and it can be utilized for various purposes.

Examples of the proximity sensor 141 may include a transmission type photoelectric sensor, a direct reflection type photoelectric sensor, a mirror-reflection type photo sensor, an RF oscillation type proximity sensor, a capacitance type proximity sensor, a magnetic proximity sensor, an infrared proximity sensor, and the like. In case where the touch screen is the capacitance type, proximity of the pointer is detected by a change in electric field according to the proximity of the pointer. In this case, the touch screen (touch sensor) may be classified as a proximity sensor.

In the following description, for the sake of brevity, recognition of the pointer positioned to be close to the touch screen will be called a 'proximity touch', while recognition of actual contacting of the pointer on the touch screen will be called a 'contact touch'. In this case, when the pointer is in the state of the proximity touch, it means that the pointer is positioned to correspond vertically to the touch screen.

By employing the proximity sensor 141, a proximity touch and a proximity touch pattern (e.g., a proximity touch distance, a proximity touch speed, a proximity touch time, a proximity touch position, a proximity touch movement state, or the like) can be detected, and information corresponding to the detected proximity touch operation and the proximity touch pattern can be outputted to the touch screen.

The audio output module 152 may convert and output as sound audio data received from the wireless communication unit 110 or stored in the memory 160 in a call signal reception mode, a call mode, a record mode, a voice recognition mode, a broadcast reception mode, and the like. Also, the audio output module 152 may provide audible outputs related to a particular function performed by the mobile terminal 100 (e.g., a call signal reception sound, a message reception sound, etc.). The audio output module 152 may include a speaker, a buzzer, or other sound generating device.

The alarm unit 153 (or other type of user notification means) may provide outputs to inform about the occurrence of an event of the mobile terminal 100. Typical events may include call reception, message reception, key signal inputs, a touch input etc. In addition to audio or video outputs, the alarm unit 153 may provide outputs in a different manner to inform about the occurrence of an event. For example, the alarm unit 153 may provide an output in the form of vibrations (or other tactile or sensible outputs). When a call, a message, or some other incoming communication is received, the alarm unit 153 may provide tactile outputs (i.e., vibrations) to inform the user thereof. Or, when a key signal is input, the alarm unit 153 may vibrate the mobile terminal 100 through a vibration unit, as a feedback of the key signal input. Through such vibration, the user can recognize the occurrence of an event. Outputs informing about the occurrence of an event may be also provided via the display unit 151 or the audio output module 152.

The haptic module 154 generates various tactile effects the user may feel. A typical example of the tactile effects generated by the haptic module 154 is vibration. The strength and pattern of the haptic module 154 can be controlled. For example, different vibrations may be combined to be outputted or sequentially outputted.

Besides vibration, the haptic module 154 may generate various other tactile effects such as an effect by stimulation such as a pin arrangement vertically moving with respect to a contact skin, a spray force or suction force of air through a jet orifice or a suction opening, a contact on the skin, a contact of an electrode, electrostatic force, etc., an effect by reproducing the sense of cold and warmth using an element that can absorb or generate heat.

The haptic module 154 may be implemented to allow the user to feel a tactile effect through a muscle sensation such as fingers or arm of the user, as well as transferring the tactile effect through a direct contact. Two or more haptic modules 154 may be provided according to the configuration of the mobile terminal 100.

The memory 160 may store software programs used for the processing and controlling operations performed by the controller 180, or may temporarily store data (e.g., a phonebook, messages, still images, video, etc.) that are inputted or outputted. In addition, the memory 160 may store a use frequency regarding respective items of the data (e.g., a use frequency of each phone number, each message, each multimedia, etc.). Also, the memory 160 may store data regarding various patterns of vibrations and audio signals outputted when a touch is inputted to the touch screen.

The memory 160 may include at least one type of storage medium including a Flash memory, a hard disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, and an optical disk. Also, the mobile terminal 100 may be operated in relation to a web storage device that performs the storage function of the memory 160 over the Internet.

The interface unit 170 serves as an interface with every external device connected with the mobile terminal 100. For example, the external devices may transmit data to an external device, receives and transmits power to each element of the mobile terminal 100, or transmits internal data of the mobile terminal 100 to an external device. For example, the interface unit 170 may include wired or wireless headset ports, external power supply ports, wired or wireless data ports, memory card ports, ports for connecting a device having an identification module, audio input/output (I/O) ports, video I/O ports, earphone ports, or the like. Here, the identification module may be a chip that stores various types of information for authenticating the authority of using the mobile terminal 100 and may include a user identity module (UIM), a subscriber identity module (SIM) a universal subscriber identity module (USIM), and the like. In addition, the device having the identification module (referred to as 'identifying device', hereinafter) may take the form of a smart card. Accordingly, the identifying device may be connected with the terminal 100 via a port. The interface unit may receive data or power from an external device and deliver the same to each of the elements in the mobile terminal 100 or transmit data within the mobile terminal 100 to an external device.

When the mobile terminal 100 is connected with an external cradle, the interface unit 170 may serve as a passage to allow power from the cradle to be supplied therethrough to the mobile terminal 100 or may serve as a passage to allow various command signals inputted by the user from the cradle to be transferred to the mobile terminal therethrough. Various command signals or power inputted from the cradle may operate as signals for recognizing that the mobile terminal is properly mounted on the cradle.

The controller 180 typically controls the general operations of the mobile terminal. For example, the controller 180 performs controlling and processing associated with voice calls, data communications, video calls, and the like. The controller 180 may include a multimedia module 181 for reproducing multimedia data. The multimedia module 181 may be configured within the controller 180 or may be configured to be separated from the controller 180.

The controller 180 may perform a pattern recognition processing to recognize a handwriting input or a picture drawing input performed on the touch screen as characters or images, respectively.

The voice recognition module 182 recognizes a voice pronounced by the user and performs a corresponding function according to the recognized voice signal.

The power supply unit 190 receives external power or internal power and supplies appropriate power required for operating respective elements and components under the control of the controller 180.

Various embodiments described herein may be implemented in a computer-readable or its similar medium using, for example, software, hardware, or any combination thereof. For hardware implementation, the embodiments described herein may be implemented by using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic units designed to perform the functions described herein. In some cases, such embodiments may be implemented by the controller 180 itself. For software implementation, the embodiments such as procedures or functions described herein may be implemented by separate software modules. Each software module may perform one or more functions or operations described herein. Software codes can be implemented by a software application written in any suitable programming language. The software codes may be stored in the memory 160 and executed by the controller 180.

Figure 2:
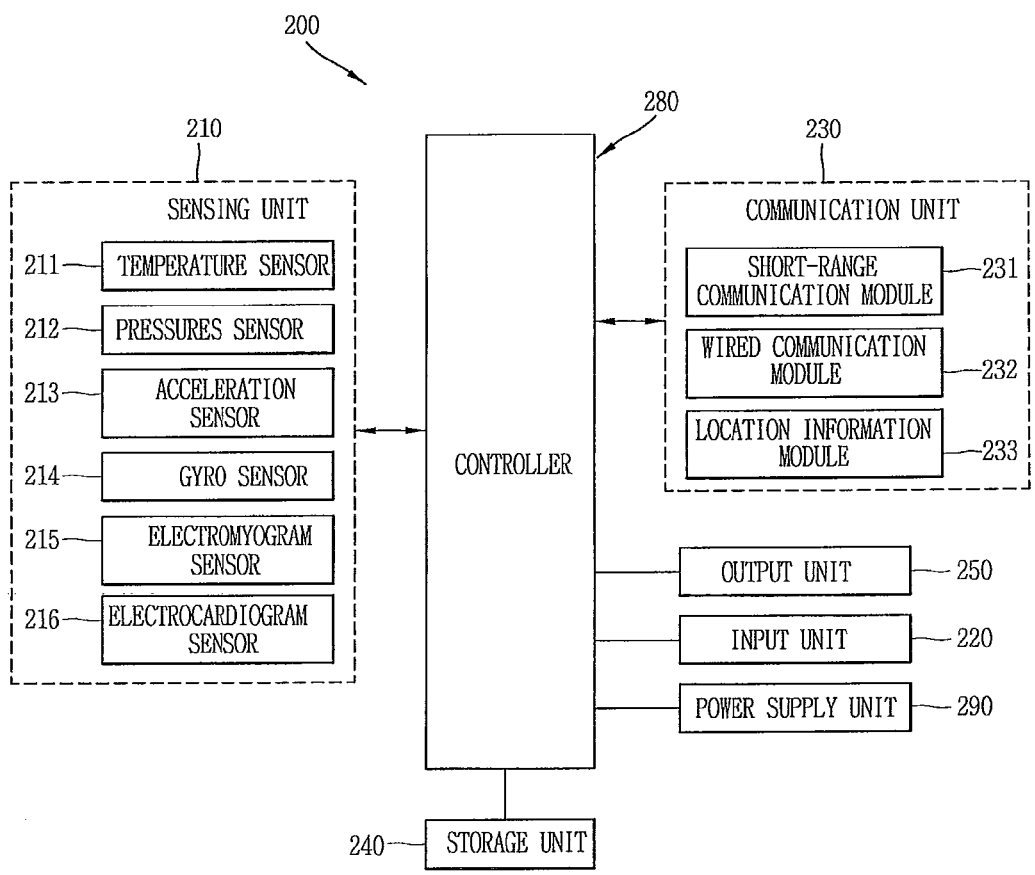
FIG. 2 is a schematic block diagram of a measurement device.

FIG. 2 is a schematic block diagram of a measurement device related to an exemplary embodiment described in the present disclosure.

As shown in FIG. 2, a measurement device 200 includes a sensing unit 210, an input unit 220, a communication unit 230, a storage unit 240, an output unit 250, a controller 280, and a power supply unit 290.

All the elements of the measurement device 200 illustrated in FIG. 2 are not essential elements, and the measurement device 200 may be implemented with more or less elements.

The measurement device 200 measures a physical condition of a subject, an object or a human body as a sensing target, and transmits the measurement information to a manager device which is to process the information. The measurement device 200 may be an agent device in compliance with a communication standard of an ISO/IEEE 11073 personal health device (PHD) with respect to health informatics, and the manager device may be a manager device in compliance with the communication standard of the PHD.

The sensing unit 210 detects a status of the subject and generates a sensing signal according to the detected status information. For example, the sensing unit 210 may include a temperature sensor 211, a pressure sensor 212, an acceleration sensor 213, a gyro sensor 214, an electromyogram sensor 215, an electrocardiogram sensor 216, and the like.

The temperature sensor 211 measures the temperature of a subject such as an object, or gas, or the like, which may be divided into a contact type temperature sensor which is brought into direct contact with the subject or an environment to measure the temperature of the subject and a non-contact type temperature sensor which measures infrared rays radiated from the subject to thus measure the temperature of the subject. The temperature sensor 211 may be implemented to measure resistance changing over temperature or detect infrared wavelength changing over temperature.

The pressure sensor 211 detects whether or not pressure is applied to the measurement device and the size of the applied pressure. The pressure sensor 212 may be divided into a mechanical pressure sensor for measuring the pressure by measuring displacement changing over pressure, a capacitance type pressure sensor for measuring the pressure by measuring the difference in displacement based on a change in capacitance between two electrodes, and an electric pressure sensor, such as a piezoresistive pressure sensor, using a piezoresistive effect of semiconductor. The pressure sensor 212 may be installed at a portion of the subject whose pressure needs to be detected.

The acceleration sensor 213 converts a change in acceleration in one direction into an electrical signal. In general, the acceleration sensor 213 may be configured to convert a change in acceleration in three-axis direction with respect to a motion of the subject into an electrical signal to thus measure acceleration of each direction.

The gyro sensor 214 measures angular velocity of the subject which makes a rotational movement. It can detect an angle at which the subject is positioned after being rotated with respect to a respective reference direction. For example, the gyro sensor 214 may detect respective rotation angles based on three-directional axes, namely, an azimuth, a pitch, and a roll.

The electromyogram sensor 215 is a module for detecting an electromyography signal generated from the muscle. It can obtain an electromyography signal through an electrode attached to the surface of the muscle.

The electrocardiogram sensor 216 measures a change in electrocardiogram formed according to the contraction of the heart of the subject. In order to measure an action potential changing according to contraction and dilatation of the heart, an electrode is attached to a part of the body of the subject and a change in potential difference over time is measured. Electrocardiogram information measured by the electrocardiogram sensor 216 may be used to measure the heart rate of the subject or discriminate an abnormal heart rhythm generated in the subject. In addition, the electrocardiogram information may be used to diagnose whether or not the subject has a coronary artery disease, whether or not the subject has a heart disorder.

The input unit 220 receives a simple input from a user required for controlling the measurement device 200. For example, the input unit 220 may be implemented in the form of one or more input buttons.

The communication unit 230 includes a short-range communication module 231 and a wired communication module 232 in order to transmit the measurement information to the manager device through the sensing unit 210, and a location information module 233 for obtaining location information of the measurement device 200.

The short-range communication module 231 is a module for communicating with the manager device within a short range. The short-range communication module 231 may support Bluetooth™, Radio Frequency IDentification (RFID), Infrared Data Association (IrDA), Ultra-WideBand (UWB), ZigBee™, wireless LAN (protocols of Bluetooth™, 802.11n, etc.) and the like. In particular, the short-range communication module 231, which is in compliance with the Bluetooth standard, may be implemented to support a Bluetooth health device profile (HDP), or the short-range communication module 231, which is in compliance with ZigBee standard, may be implemented to support a personal, home and hospital care (PHHC) profile.

The wired communication module 232 is a module for transmitting the measurement information through a cable connected to the manager device. For example, the wired communication module 232, which is in compliance with a universal serial bus (USB) standard, may be implemented to support a personal health device class (PHDC).

The location information module 233 obtains or checks the location of the measurement device 200. For example, the location information module 233 may be a global positioning system (GPS) module for receiving location information from a plurality of artificial satellites. Here, the location information may include coordinate information represented by latitude and longitude. For example, the GPS module may measure an accurate time and distance from three or more satellites, and accurately calculate a current location of the mobile communication terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites. As the location information module 233, a Wi-Fi position system and/or hybrid positioning system may be used.

The storage unit 240 may store programs or data required for the operation of the controller 280. When communication with the manager device is not available, detection information regarding the subject measured by the sensing unit 210 may be temporarily stored in the storage unit 240. The storage unit 240 may be an embedded memory type unit or a removable media type unit.

The output unit 250 serves to simply output information whether or not the measurement device 200 operates or an operational state of the measurement device 200. For example, the output unit 250 may be implemented in the form of a display for visually display information, or a lamp.

The controller 280 is a module for converting analog information, e.g., temperature information, pressure information, acceleration information, angular velocity information, electromyogram information, electrocardiogram information, and the like, measured by the sensing unit 210 into digital information, and serves to control various elements of the measurement device 200. In particular, the controller 280 may serve to convert the digital information into a message format that the manager device can understand, e.g., a protocol in compliance with a standard of an ISO/IEEE P11073-10441 Device specialization—Cardiovascular fitness and activity monitor.

The power supply unit 290 may be a power source with battery cell embedded inside, a receiver module using a wireless power signal or a power module using an environmental power source such as a converted power from an impact on the power supply of the measurement device 200 itself.

The configuration and use status of the exercise guide apparatus according to an exemplary embodiment of the present disclosure will now be described with reference to FIGS. 3 to 6.

Figure 3:
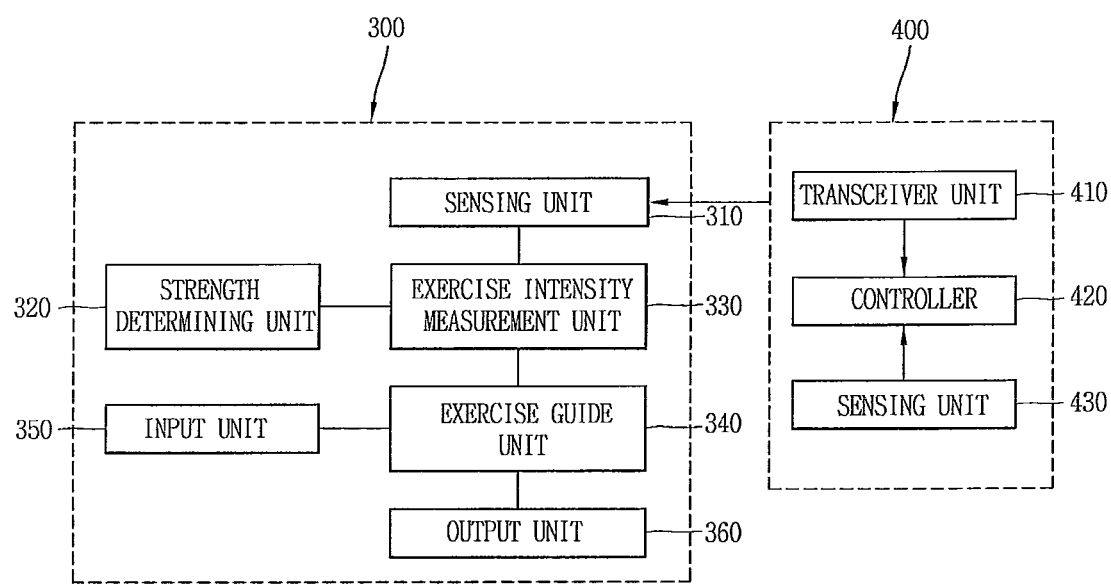
FIG. 3 is a schematic block diagram of an exercise guide apparatus.
Figure 4:
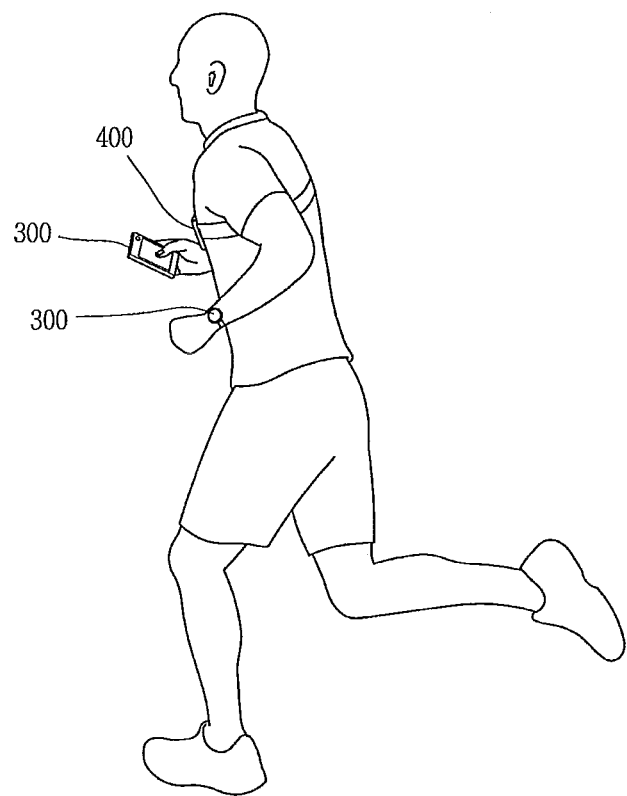
FIG. 4 is a view for explaining a usage state of an exercise guide apparatus 300 and a measurement device 400 according to an exemplary embodiment of the present invention.

FIG. 3 is a schematic block diagram of an exercise guide apparatus 300 according to an exemplary embodiment of the present disclosure and FIG. 4 is a view for explaining a usage state of an exercise guide apparatus 300 and a measurement device 400 according to an exemplary embodiment of the present disclosure.

The exercise guide apparatus 300 according to an exemplary embodiment of the present disclosure provides guide information regarding an exercise intensity or an exercise pattern based on fat oxidation rate of a subject who is exercising such as running, or the like. To this end, the exercise guide apparatus 300 determines a current exercise intensity of the subject, estimates a fat oxidation rate by comparing the determined current exercise intensity with a maximal oxygen consumption or maximal oxygen uptake (VO2max), and provides exercise guide information based on the estimated fat oxidation rate.

In general, in order to measure a fat oxidation rate, a method for analyzing a respiratory gas on the assumption that a nitrogen output through urine is negligible may be used, but in the present exemplary embodiment, the exercise guide apparatus 300 estimates a fat oxidation rate by using a fat oxidation curve based on exercise intensity.

The exercise guide apparatus 300 may be configured include a sensing unit 310, a strength determining unit 320, an exercise intensity measurement unit 330, an exercise guide unit 340, an input unit 350, and an output unit 360.

The sensing unit 310 obtains heart rate information of the subject. For example, with reference to FIG. 4, the heart rate information may be obtained by the measurement device 400, apart from the exercise guide apparatus 300 according to an exemplary embodiment of the present disclosure. In this case, the sensing unit 310 included in the exercise guide apparatus 300 may be implemented in the form of a communication module for receiving the heart rate information from the measurement device 400.

The measurement device 400 delivering the heart rate information to the exercise guide apparatus 300 may include a sensing unit 430 including an electrocardiogram sensor for measuring a change in electrocardiogram of the subject through an electrode attached to a part of the subject's body during the exercise such as running, or the like, a controller 420 for converting electrocardiogram information, i.e., analog information, measured by the sensing unit 430 into digital information and measuring a heart rate by using the electrocardiogram information, and a transceiver unit 410 for transmitting the electrocardiogram information or the heart rate information to the exercise guide apparatus 300, i.e., a manager device. The measurement device 400 may be implemented in the form of the measurement device 200 as shown in FIG. 2.

Meanwhile, in the exercise guide apparatus according to a modification of the present disclosure, the sensing unit 310 may be configured to measure a change in the electrocardiogram of the subject through the electrode attached to the subject and converted the measured change in the electrocardiogram into digital information to thus directly obtain heart rate information of the subject. In the exercise guide apparatus according to a modification of the present disclosure, the sensing unit 310 may be configured in the form of an electrocardiogram sensor or a heart rate sensor for obtaining heart rate information by measuring a change in the electrocardiogram of the subject from the electrode attached to a part of the subject's body.

The strength determining unit 320 determines a maximal oxygen consumption or maximal oxygen uptake (VO2max) of the subject. The maximal oxygen consumption or maximal oxygen uptake (VO2max) denotes a maximal amount of oxygen which can be used through inhalation by the subject, which is used as a value indicating the subject's body strength. The strength determining unit 320 may use a generally known method in order to determine the maximal oxygen consumption of the subject.

The exercise intensity measurement unit 330 determines a current exercise intensity of the subject based on the heart rate obtained by the sensing unit.

The exercise intensity may be determined in consideration of physical condition of the subject, such as gender, age, weight, and the like. For example, the exercise intensity of the subject may be determined in consideration of a maximum heart rate (MHR) according to age, among the physical conditions of the subject. In detail, current exercise intensity of the subject may be determined by Equation 1 shown below:

$$MHR(beats/min.)=208-(0.7\times age) \quad \text{[Equation 1]}$$

The exercise intensity measurement unit 330 may determine an exercise intensity by using the maximum heart rate, and in this case, the formula representing the relationship between the maximum heart rate and the exercise intensity may be used. For example a current exercise intensity of the subject may be determined by using such a formula as Equation 2 shown below:

$$\text{Exercise intensity}=1.5472\times\% \text{ MHR} \quad \text{[Equation 2]}$$

The exercise guide unit 340 estimates a fat oxidation rate (%VO2max) of the subject based on the determined current exercise intensity of the subject. The fat oxidation rate refers to a rate of fat oxidation according to the current exercise intensity to the maximal oxygen consumption (VO2max), and when the maximal oxygen consumption (VO2max) is determined in consideration of the physical conditions of the subject who is exercising, the fat oxidation rate of the subject refers to an exercise intensity of the subject at that time.

In order to estimate the fat oxidation rate, the exercise guide unit 340 uses a curve indicating fat oxidation according to the exercise intensity. Hereinafter, a fat oxidation curve used to estimate the fat oxidation rate and a method for determining it will now be described.

Figure 5:
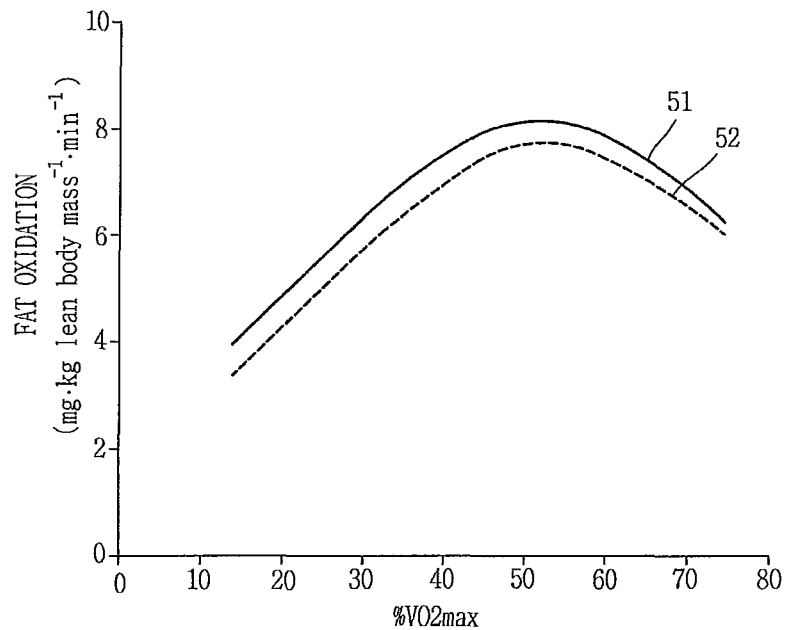
FIG. 5 shows an example of fat oxidation curves.

The exercise guide unit 340 determines a fat oxidation curve to be used to estimate a fat oxidation rate according to a method of selecting a fat oxidation curve corresponding to the physical information of the subject from a database containing fat oxidation patterns. As shown in FIG. 5, the database containing fat oxidation patterns refers to an aggregate including fat oxidation curves 51 and 52 formed to be different according to various physical conditions. For example, the fat oxidation curves in the database containing fat oxidation patterns may be curves representing fat oxidation corresponding to an exercise intensity according to respective physical conditions.

The exercise guide unit 340 determines a fat oxidation curve fitting the physical information of the subject received from the input unit 350 among the fat oxidation curves stored in the database containing fat oxidation patterns. For example, the exercise guide unit 340 may selectively receive at least one among the conditions such as the subject's age, gender, weight, and the like, through the input unit 350, or may determine a fat oxidation curve according to pre-set physical conditions.

Figure 6:
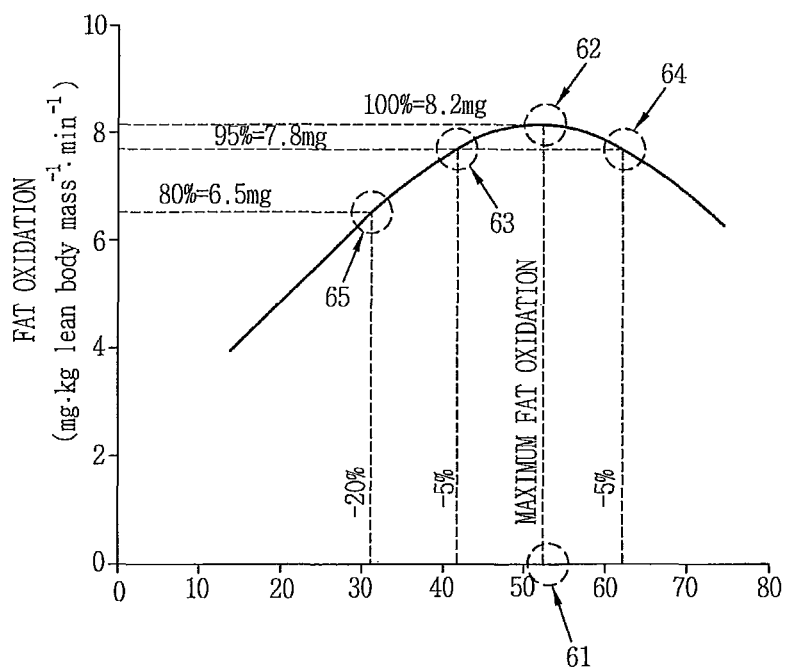
FIG. 6 shows an example of a fat oxidation curve used in the exercise guide apparatus.

FIG. 6 is a graph showing an example of a fat oxidation curve used in the exercise guide apparatus according to an exemplary embodiment of the present disclosure. A fat oxidation and a fat oxidation rate appearing on the determined fat oxidation curve will now be described with reference to FIG. 6.

The exercise guide unit 340 determines a fat oxidation curve corresponding to the physical information of the subject from the database containing fat oxidation patterns. FIG. 6 shows an example of a determined fat oxidation curve of a male adolescent of a normal weight.

With reference to FIG. 6, the when an exercise intensity on the fat oxidation curve according to an exercise intensity is near 50% VO2max (61), a maximum fat oxidation 62 is obtained, and the case in which the maximum fat oxidation 62 is obtained is defined as a fat oxidation rate of 100%. The fat oxidation curve has such a form that the fat oxidation is reduced before and after the exercise intensity 61 representing the maximum fat oxidation 62. Thus, the fat oxidation rate is reduced in case of an exercise intensity which is stronger or weaker than the exercise intensity 61 representing the maximum fat oxidation 62.

For example, when the exercise intensity of the subject indicates a fat oxidation rate of 95%, it corresponds to 95% of fat oxidation over the maximum fat oxidation corresponds the part (63 and 64), so the exercise intensities which are stronger and weaker than the exercise intensity 61 indicating the maximum fat oxidation exhibit a fat oxidation which is insufficient 5%.

The exercise guide unit 340 estimates a current fat oxidation rate of the subject by calculating fat oxidation according to the current exercise intensity over the maximum fat oxidation by using the determined fat oxidation curve. Also, the exercise guide unit 340 may output the estimated fat oxidation rate, fat oxidation, the accumulated fat oxidation, and the like, to the output unit 360.

In addition, the exercise guide unit 340 compares a particular threshold value of an oxidation rate indicating that fat is being effectively oxidized and the estimated fat oxidation rate to determine whether or not the estimated fat oxidation rate is greater than the threshold value.

For example, with reference to FIG. 6, when a threshold value indicating an effective fat oxidation rate of the exercise guide unit 340 is set to be 80%, the exercise guide unit 340 compares the threshold value 80% (65) and a fat oxidation rate estimated according to the current exercise intensity of the subject, and determines whether or not the estimated fat oxidation rate is greater than the effective fat oxidation rate, namely, whether or not the current exercise intensity is 30%

VO2max or greater on the fat oxidation curve corresponding to the physical conditions of the subject according to the comparison results.

The exercise guide unit 340 may provide exercise guide information helping the user take an exercise intensity or an exercise pattern based on the estimated fat oxidation rate.

Namely, in case of providing exercise guide information regarding an exercise intensity by the exercise guide unit 340, the exercise guide unit 340 may provide exercise guide information according to which the user may control the exercise intensity such that the fat oxidation rate of the subject is maintained within the range of a particular fat oxidation rate. This is because, when the measured exercise intensity increases, calorie consumption may be increased accordingly, but fat oxidation is made along the fat oxidation curve having such a form as shown in FIG. 6. For example, the exercise guide unit 340 can provide exercise guide information recommending the user to control his exercise intensity such that the estimated fat oxidation rate is a minimum 80% at the left side and a maximum 95% at the right side based on the exercise intensity 61 indicating the maximum fat oxidation.

Also, in case of providing exercise guide information regarding an exercise pattern by the exercise guide unit 340, the exercise guide unit 340 can provide exercise guide information such that the user may repeat exercise patterns involving high intensity exercise that is gradually changed to low intensity exercise.

Meanwhile, the exercise guide apparatus 300 according to an exemplary embodiment of the present disclosure may be applicable to the mobile terminal 100 as described above with reference to FIG. 1. Namely, the mobile terminal 100 employing the exercise guide apparatus according to an exemplary embodiment of the present disclosure may be configured to include a wireless communication unit 110 for obtaining electrocardiogram information measured by the measurement device and a controller 180 for determining a maximum oxygen consumption and a current exercise intensity of the subject, estimating a fat oxidation rate of the subject, and providing control to generate exercise guide information based on the estimated fat oxidation rate. The mobile terminal 100 employing the exercise guide apparatus according to an exemplary embodiment of the present disclosure operates as described above with reference to FIG. 3, so a detailed description thereof will be omitted.

Hereinafter, a method for providing exercise guide information regarding an exercise intensity and an exercise pattern based on a fat oxidation rate by the exercise guide apparatus according to an exemplary embodiment of the present disclosure will be described with reference to FIG. 7. Also, a method for outputting exercise guide information generated by the exercise guide apparatus will be described with reference to FIGS. 8 and 9.

Figure 7:
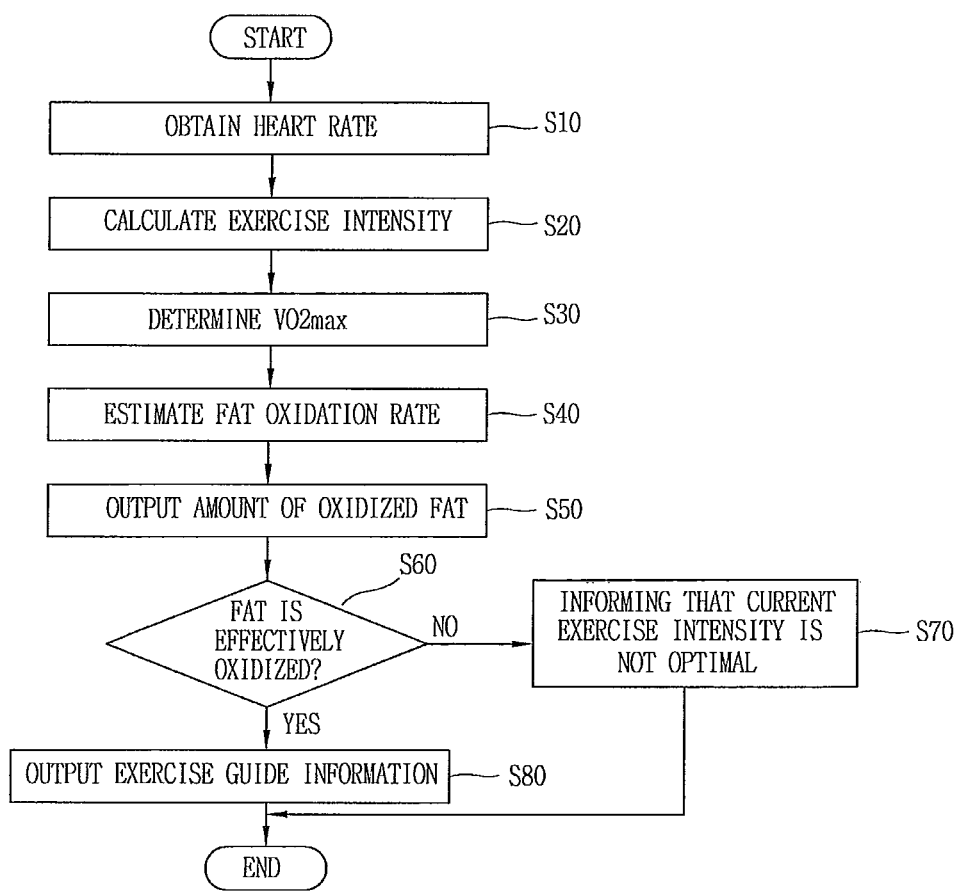
FIG. 7 is a flow chart illustrating the process of a method for providing exercise guide information.
Figure 8:
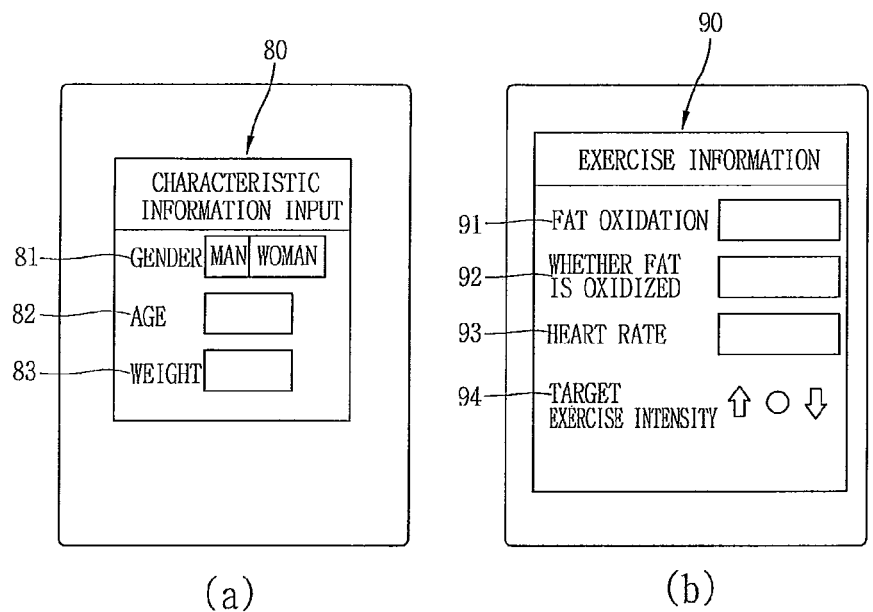
FIG. 8 shows a display screen of the exercise guide apparatus.

FIG. 7 is a flow chart illustrating the process of a method for providing exercise guide information according to an exemplary embodiment of the present disclosure, and FIG. 8 shows a display screen of the exercise guide apparatus according to an exemplary embodiment of the present disclosure.

First, the exercise guide apparatus obtains a heart rate of the subject (step S10). The heart rate information may be measured by the measurement device, a device separated from the exercise guide apparatus, and received by the communication module, or may be directly obtained by using the electrocardiogram sensor included in the exercise guide apparatus.

Next, the exercise guide apparatus determines a current exercise intensity of the subject based on the obtained heart rate (step S20) and determines a maximal oxygen consumption of the subject (step S30). The maximal oxygen consumption may be determined based on the maximum heart rate of the subject. Also, the exercise guide apparatus may use characteristic information of the subject received by the input unit to determine the maximal oxygen consumption. For example, with reference to FIG. 8(*a*), the exercise guide apparatus may display a screen image 80 for receiving characteristic information on the output unit, receive a signal for inputting at least one of respective items of characteristic information, namely, gender (81), age (82), and weight (83), and use the received signal in determining the maximal oxygen consumption.

Also, the exercise guide apparatus estimates a fat oxidation rate of the subject (step S40) and outputs the amount of oxidized fat of the subject (step S50).

In order to estimate the fat oxidation rate, the exercise guide apparatus may use a fat oxidation curve. Namely, the exercise guide apparatus prepares a database containing fat oxidation patterns including respective fat oxidation curves according to the characteristic information, and selects a fat oxidation curve corresponding to the characteristic information of the subject which has been received by the input unit or previously set, from the database containing fat oxidation patterns.

The characteristic information of the subject may be at least one of gender, age, and weight of the subject. For example, the characteristic information may be received through the characteristic information input screen image 80 illustrated in FIG. 8(*a*) or may be previously input in a previously stage and set.

Thereafter, the exercise guide apparatus calculates the ratio of the fat oxidation corresponding to a current exercise intensity to the maximum fat oxidation corresponding to the determined maximal oxygen consumption to estimate a fat oxidation rate. The exercise guide apparatus may display the estimated fat oxidation rate on the output unit.

The exercise guide apparatus may accumulate fat oxidation of the subject and display the accumulated fat oxidation on the output unit. To this end, the exercise guide apparatus may obtain time which has been accumulated since the fat of the subject started to be oxidized, calculate an amount of oxidized fat accumulated during the accumulated lapse time, and output the accumulated amount of oxidized fat.

Next, the exercise guide apparatus determines whether or not the fat of the subject has been effectively oxidized (step S60). In this process, whether or not the estimated fat oxidation rate is greater than a threshold value on the determined fat oxidation curve is determined. The exercise guide apparatus generates exercise guide information according to the determination results and output the generated exercise guide information to the output unit.

Namely, when the estimated fat oxidation rate is smaller than the threshold value according to the determination results, the exercise guide apparatus may inform the user that a current exercise intensity is not optimal (step S70). Meanwhile, when the estimated fat oxidation rate is equal to or greater than the threshold value according to the determination results, namely, when the fat of the subject is being effectively oxidized, the exercise guide apparatus generates exercise guide information regarding the exercise intensity and exercise pattern based on the estimated fat oxidation rate and outputs the generated exercise guide information (step S80).

For example, with reference to FIG. 8(*b*), the exercise guide apparatus may display an exercise guide information screen image 90 on the output unit. The exercise guide information screen image 90 may include the accumulated amount of oxidized fat 91, whether or not fat is being effectively oxidized 92, a current heart rate 93, a target 94 of the exercise intensity, and the like. As for the target of the exercise intensity, information recommending the user to do exercise with an exercise intensity stronger than the current exercise intensity, recommending the user to maintain the current exercise intensity, or recommending the user to do exercise with an exercise intensity weaker than the current exercise intensity.

Figure 9:
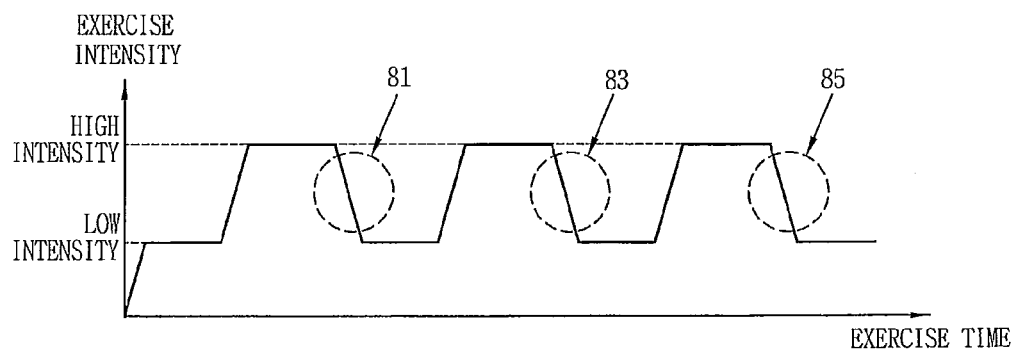
FIG. 9 shows a method for providing exercise guide information regarding an exercise pattern by the exercise guide apparatus.

FIG. 9 is a graph showing a method for providing exercise guide information regarding an exercise pattern by the exercise guide apparatus according to an exemplary embodiment of the present disclosure.

In providing exercise guide information regarding an exercise pattern by the exercise guide unit 340, the exercise guide unit 340 can provide exercise guide information such that the user may repeat exercise patterns 81, 83, and 85 involving high intensity exercise that is gradually changed to low intensity exercise.

This is because, stimulations required for lypolysis intensively works during high intensity exercise, but when the exercise intensity is gradually changed to low intensity exercise, free fatty acid components raising the fat oxidation rate are increased.

The respective exercise methods according to exemplary embodiments according to the present disclosures as described above may be implemented in the form of programs which can be executed by various computer means, and recorded on a computer-readable medium. The computer-readable medium may include program commands, data files, data structures, alone, or a combination thereof. Program instructions recorded on the medium may be particularly designed and structured for the present disclosure or available to those skilled in computer software.

Examples of the computer-readable recording medium include hardware devices, particularly configured to store and perform program commands, such as, magnetic media, such as a hard disk, a floppy disk, and a magnetic tape; optical media, such as a compact disk-read only memory (CD-ROM) and a digital versatile disc (DVD); magneto-optical media, such as floptical disks; a read-only memory (ROM); a random access memory (RAM); and a flash memory. Program commands may include, for example, a high-level language code that can be executed by a computer using an interpreter, as well as a machine language code made by a complier. The hardware devices may be configured to be operated by one or more software modules to implement the present disclosure, and vice versa.

As the present disclosure may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

The invention claimed is:

1. An exercise guide apparatus comprising:
a sensing unit configured to obtain a heart rate of a subject;
a strength determining unit configured to determine a maximal oxygen uptake of the subject;
an exercise intensity measurement unit configured to determine a current exercise intensity of the subject based on the heart rate obtained by the sensing unit; and
an exercise guide unit configured to estimate a fat oxidation rate of the subject, determine whether or not fat oxidation of the subject occurs, generate guide information according to a result of the determination of the occurrence of fat oxidation, and display the guide information generated,
wherein the fat oxidation rate is estimated based on a ratio of fat being oxidized at the current exercise intensity to the maximal oxygen uptake, and
wherein the occurrence of fat oxidation is determined by checking whether or not the fat oxidation rate estimated is greater than a threshold.

2. The apparatus of claim 1, wherein if the fat oxidation is determined not to occur, the guide information generated by the exercise guide indicates that the current exercise intensity is not optimal for fat oxidation.

3. The apparatus of claim 1, wherein the exercise guide unit selects a fat oxidation curve corresponding to characteristic information of the subject from a database containing fat oxidation patterns, and estimates the fat oxidation rate by using the fat oxidation curve selected.

4. The apparatus of claim 3, further comprising:
an input unit configured to receive an input signal,
wherein the exercise guide unit prepares the database containing the fat oxidation patterns by characteristic information, receives characteristic information of the subject by the input signal, and selects the fat oxidation curve corresponding to the characteristic information received from the database, and
wherein the characteristic information of the subject is at least one of gender, age, and weight.

5. The apparatus of claim 3, further comprising:
a timer unit configured to accumulate a time,
wherein if the fat oxidation is determined to occur, the exercise guide unit obtains the accumulated total time of the heart rate obtainment from the timer unit, calculates an accumulated fat oxidation during the accumulated total time, and displays the accumulated fat oxidation, and
wherein the accumulated fat oxidation is calculated by using a value on the fat oxidation curve corresponding to the fat oxidation rate estimated.

6. The apparatus of claim 1, wherein the strength determining unit determines the maximal oxygen uptake based on a maximum heart rate of the subject.

7. The apparatus of claim 1, wherein the sensing unit obtains the heart rate of the subject from an electrocardiogram sensor.

8. A method for providing exercise guide information, the method comprising:
obtaining a heart rate of a subject;
determining a current exercise intensity of the subject based on the heart rate;
determining a maximal oxygen uptake of the subject;
estimating a fat oxidation rate of the subject, the fat oxidation rate indicating a ratio of fat being oxidized at the current exercise intensity to the maximal oxygen uptake;
determining whether or not fat oxidation of the subject occurs by checking whether or not the fat oxidation rate estimated is greater than a threshold;
generating guide information according to a result of the determination of the occurrence of fat oxidation; and
displaying the guide information.

9. The method of claim 8, wherein if the fat oxidation is determined not to occur, the guide information generated indicates that the current exercise intensity is not optimal for fat oxidization.

10. The method of claim 8, wherein the estimating of the fat oxidation rate comprises:
- selecting a fat oxidation curve corresponding to characteristic information of the subject from a database containing fat oxidation patterns; and
- determining whether or not the fat oxidation rate estimated is greater than a threshold on the fat oxidation curve selected.

11. The method of claim 10, wherein the selecting the fat oxidation curve further comprises:
- preparing the database containing the fat oxidation patterns by characteristic information; and
- receiving characteristic information of the subject by an input signal,
- wherein the characteristic information of the subject is at least one of gender, age, and weight.

12. The method of claim 10, further comprising:
- obtaining an accumulated total time of the heart rate obtainment if the fat oxidation is determined to occur;
- calculating an accumulated fat oxidation during the accumulated total time by using a value on the fat oxidation curve corresponding to the fat oxidation rate estimated; and
- displaying the accumulated fat oxidation.

* * * * *